US008163796B1

(12) United States Patent
Johnson et al.

(10) Patent No.: US 8,163,796 B1
(45) Date of Patent: Apr. 24, 2012

(54) TREATMENT OF CANCER BY OXIDATION-REDUCTION POTENTIATION OF CANCEROSTATIC DICARBONYLS

(75) Inventors: Morris A. Johnson, Greenville, WI (US); Michael M. Smits, Appleton, WI (US)

(73) Assignee: BioChemical Solutions, LLC, Appleton, WI (US)

( * ) Notice: Subject to any disclaimer, the term of this patent is extended or adjusted under 35 U.S.C. 154(b) by 0 days.

(21) Appl. No.: 12/804,376

(22) Filed: Jul. 20, 2010

Related U.S. Application Data

(60) Provisional application No. 61/271,902, filed on Jul. 28, 2009.

(51) Int. Cl.
*A01N 43/08* (2006.01)
*A01N 43/36* (2006.01)
*A01N 37/08* (2006.01)
*A61K 31/34* (2006.01)
*A61K 31/40* (2006.01)
*A61K 31/215* (2006.01)

(52) U.S. Cl. .................. 514/472; 514/423; 514/530

(58) Field of Classification Search ................ None
See application file for complete search history.

(56) References Cited

U.S. PATENT DOCUMENTS

| 4,238,500 | A | 12/1980 | Szent-Gyorgyi | |
|---|---|---|---|---|
| 5,476,966 | A | 12/1995 | Anderson | |
| 5,849,783 | A | 12/1998 | Egyud | |
| 5,888,552 | A | 3/1999 | Bounous | |
| 5,969,174 | A | 10/1999 | Creighton | |
| 6,407,071 | B1 | 6/2002 | Rubin | |
| 6,576,660 | B1 * | 6/2003 | Liao et al. | 514/456 |
| 6,613,793 | B2 * | 9/2003 | Burman et al. | 514/423 |
| 6,756,063 | B2 * | 6/2004 | Kiss | 424/630 |
| 7,271,161 | B2 | 9/2007 | Siddik | |
| 7,858,659 | B2 | 12/2010 | Hoffman | |
| 2008/0188541 | A1 | 8/2008 | Ray | |

FOREIGN PATENT DOCUMENTS

| WO | WO2007109184 | 9/2007 |
|---|---|---|
| WO | WO2008082579 | 7/2008 |
| WO | WO2010028503 | 3/2010 |

OTHER PUBLICATIONS

Immordino, Stealth liposomes: review of the basic science, rationale, and clinical applications, existing and potential, Int J Nanomedicine, Sep. 2006, 297-315, 1(3).
Zamboni, Concept and Clinical Evaluation of Carrier-Mediated Anticancer Agents, The Oncologist, 2008, 248-260,13.
Haslett, Why is apoptosis important to clinicians?, BMJ, 2001, 1499-1500, 322.
Kasibhatla, Why Target Apoptosis in Cancer Treatment?, Molecular Cancer Therapeutics, Jun. 2003, 573-580, 2.
Conger, Source of cancer stem cell resistance to radiation discovered at Stanford, Stanford School of Medicine, News Release, Feb. 4, 2009.
Trachootham, Targeting cancer cells by ROS—mediated mechanisms: a radical therapeutic approach?, Drug Discovery, Jul. 2009, 579-591, 8.
Dai, Malignant Cells Can Be Sensitized to Undergo Growth Inhibition and Apoptosis by $AsO_3$ Through Modulation of the Glutathione Redox System, Blood,Jan. 1999, 268-277, 93:1.
Schnelldorfer, Glutathione Depletion Causes Cell Growth Inhibition and Enhanced Apoptosis in Pancreatic Cancer Cells, Cancer Oct. 1, 2000, 1440-1447, 89:7.
Freisen, A critical role of glutathione in determining apoptosis sensitivity and resistance in leukemia cells, Cell Death and Differentiation, 2004, S73-S85, 11.
Apple, Arrest of Cancer in Mice by Therapy With Normal Metabolites. Cancer Chemotherapy Reports, Dec. 1968, 687-696, 52:7.
Szent-Gyorgyi, Cell Division, SH, Ketoaldehydes, and Cancer, PNAS, 1966,388-393, 55:2.
Milanesa, Methylglyoxal-Induced Apoptosis in Human Prostate Carcinoma: Potential Modality for Prostate Cancer Treatment, Eur Urol, 2000, 728-734, 37.
Talukdar, Treatment of a number of cancer patients suffering from different types of malignancies by methylglyoxal-based formulations, Cancer Therapy, 2006, 205-222,4.
Talukdar, A brief critical overview on the biological effects of methylglyoxal in treating cancer patients, Drug Metabolism and Drug Interactions, 2008, 175-210, 23:1-2.
Ghosh, In vivo assessment of toxicity and pharmacokinetics of methylglyoxal , Toxicology and Applied Pharmacology 2006, 45-58,212.
Kennedy, The use of a Whey Protein Concentrate in the Treatment of Patients with Metastatic Carcinoma, Anticancer Research, 1995, 2643-2650, 15.
Bounous, Whey Protein Concentrate (WPC) and Glutathione Modulation in Cancer Treatment, Anticancer Research, 2000, 4785-4792, 20.
Agarwal, N-Acetyl-Cysteine Promotes Angiostatin Production and Vascular Collapse in an Orthotopic Model of Breast Cancer, Am J Path, May 2004, 1683-1696, 164:5.
Lee, Depletion of tumor versus normal tissue glutathione by buthionine sulfoximine, Br J Cancer, 1987, 33-38, 56.

(Continued)

Primary Examiner — Robert M Kelly

(57) ABSTRACT

A novel treatment regimen is described for the control and elimination of cancer cell populations including cancer stem cells. The disclosed protocol consists of a pretreatment step followed by a treatment step. The pretreatment step sensitizes cancer cells to apoptosis by altering their intracellular oxidation-reduction state via reduced glutathione depletion. The treatment step involves the sequential administration of a cancerostatic dicarbonyl compound to induce apoptosis. The use of nanoparticle delivery systems further enhances both the pharmacokinetic and pharmacodynamic properties of the pretreatment compounds and the cancerostatic dicarbonyls. Since the pretreatment and treatment compounds are carefully selected and delivered, normal cells are not affected and side effects are kept to a minimum.

5 Claims, No Drawings

OTHER PUBLICATIONS

Fekete, Rate of Buthionine Sulfoximine Entry into Brain and Xenotransplanted Human Gliomas, Cancer Research, Feb. 15, 1990, 1251-1256, 50.

Lee, Effects of Buthionine Sulfoximine Treatment on Cellular Glutathione Levels and Cytotoxicities in Human Stomach and Ovarian Cancer, Kor J Int Med, Jul. 1992,11-117, 7,2.

Anderson, Depletion of Glutathione by Buthionine Sulfoximine is Cytotoxic for Human Neuroblastoma Cell Lines via Apoptosis, Exp Cell Res, 1999, 183-192, 246.

Rudin, Inhibition of Glutathione Synthesis Reverses Bcl-2-mediated Cisplatin Resistance, Cancer Research, Jan. 15, 2003, 312-318, 63.

Fang, Cytotoxic Effect of trans-Cinnamaldehyde from *Cinnamomum osmophloeum* Leaves on Human Cancer Cell Lines, Int J Appl Sc & Eng, 2004, 136-147, 2:2.

Karunagaran, Induction of Apoptosis by Curcumin and its Implications for Cancer Therapy, Current Cancer Drug Targets, 2005, 117-129, 5.

Gibellini, Interfering with ROS Metabolism in Cancer Cells: The Potential Role of Quercetin, Cancer, Jun. 14, 2010, 1288-1311, 2.

Thomson, Phenethyl Isothiocyanate Triggers Apoptosis in Jurkat Cells Made Resistant by the Overexpression of Bcl-2, Cancer Res, Jul. 1, 2006, 6772-6777, 66:3.

Smits, Methylglyoxal: Enzyme Distributions Relative to its Presence in Douglas-fir Needles and Absence in Douglas-fir Callus, Arch Biochem Biophy, May 1981, 431-439, 208:2.

Earnshaw, The Effect of Glutathione on Development in Wild Carrot Suspension Cultures, Biochemical and Biophysical Research Communications, Dec. 31, 1985, 988-993, 133:3.

\* cited by examiner

TREATMENT OF CANCER BY OXIDATION-REDUCTION POTENTIATION OF CANCEROSTATIC DICARBONYLS

CROSS-REFERENCE TO RELATED APPLICATIONS

This patent application claims priority to U.S. Provisional Patent Application No. 61/271,902, filed Jul. 28, 2009, which provisional patent application is also incorporated herein by reference in its entirety by the present inventors.

FEDERALLY SPONSORED RESEARCH

Not Applicable

SEQUENCE LISTING OR PROGRAM

Not Applicable

FIELD OF THE INVENTION

The present invention relates to a protocol for selectively controlling and eliminating cancer cells without harming normal cells or causing harmful side effects. The invention combines the use of various biologically active compounds and corresponding delivery systems to induce apoptosis by depleting intracellular reduced glutathione (GSH) levels in synergy with cancerostatic dicarbonyls. The invention relates to all types and stages of cancer in animals including mammals and humans. The anticancer activity of this protocol may be augmented by surgery or radiation treatments.

BACKGROUND OF THE INVENTION

Cancer is currently treated primarily with one of the following three types of therapies: surgery, radiation or chemotherapy. Frequently a combination of two or more of the therapies are prescribed in order to optimize the probability of a successful outcome.

Surgery is the traditional approach whereby all or part of a tumor mass is removed. Surgery is typically only effective for treating cancers in their earlier stages. Surgery is also limited to localized masses that are accessible to the surgeon and are not disseminated cancers like leukemia for example. Statistics have shown that, for more than 50% of cancer patients, by the time they are diagnosed surgery is no longer an effective treatment. Surgical procedures are also thought to increase the chances of metastases by dislodging small colonies of cells into the bloodstream. Most cancer patients do not die from surgery but rather from the subsequent metastasis and recurrence of cancer.

Radiation, much like surgery, is effective when the cancer is diagnosed in the early to mid stages and the disease is localized in a defined region of the body. This allows a maximal dose to be focused on the proliferative tissue while minimizing the exposure to adjoining normal tissue. In practice it is extremely difficult to shield the nearby normal tissue from the cytotoxic effects of the radiation and still deliver a therapeutic dose. An additional complication of radiation is the induction of radiation resistant cells during the course of treatment. Thus even the best radiotherapeutic techniques often result in incomplete tumor reduction and subsequent recurrence.

Chemotherapy has historically been designed to attack either rapidly dividing cells or cell metabolism. Based on its ability to permeate throughout most body tissues, it holds, in theory at least, the ability to address metastases. Although it can be effective, the side effects from these toxic compounds can be severe, e.g., vomiting, hair loss, weight loss, and immune system suppression through depleted white blood cell counts. Because of the severe side effects, many patients cannot successfully complete the entire cycle of treatment. Some cancer patients even die from the chemotherapy-induced side effects.

Chemotherapy in spite of these obstacles achieves complete remission in many patients. Based on available means of assessing the cancer burden in the body, they appear to be cured. However, a high percentage of these same patients experience relapse and death due to the cancer. For the individual patient there are many mechanisms which may ultimately render the chemotherapeutics ineffective. Chief among them are the pharmacokinetics which are manifested in bioavailability and distribution and the pharmacodynamics which are manifested in the mechanism of cell death and drug resistance. Furthermore, the recent discovery of cancer stem cells and their proposed role in driving and maintaining tumor growth and metastasis, adds one further level of complexity to the problem.

Bioavailability is the percentage of an administered dose of unchanged drug which reaches the systemic circulation. While the ease of administration of oral cancerostatic drugs is extremely attractive, the bioavailability is typically very low and inconsistent from person to person. This is due to the fact that the absorption of anticancer drugs in the gastrointestinal tract is incomplete and the drugs themselves can be chemically modified to an inactive form. Once in the bloodstream, the drugs are immediately confronted with hepatic first pass metabolism in addition to toxic removal systems such as glutathione-S-transferase. Oral administration therefore makes dosing calculations very difficult and targeting typically nonspecific. While much research is currently focused on oral, oral buccal, oral sublingual and transdermal drug delivery systems, intravenous administration is often necessary in order to approach 100% bioavailability of cancerostatic drugs.

Distribution is the dispersion or dissemination of substances throughout the fluids and tissues of the body. Many chemotherapeutics upon entrance to the systemic circulation become evenly distributed and based, on their mechanism of action, begin to work on both normal and cancer cells. This nonspecific, nontargeted delivery results in the typical severe side effects and thus limits the dosing to a rather small therapeutic window. Recent advances like drug encapsulation in antitumor liposomes, attachment to albumin particles, and antibody ligand surface binding have improved distribution and targeting issues. In particular, antitumor liposomes administered by (IV) (intravenous) provide high bioavailability, encapsulation protection from metabolism, long systemic circulation times due to pegylation, and passive and active targeting through EPR (Enhanced Permeation and Retention) and surface decoration [1, 2].

The mechanism of action for the vast majority of currently available anticancer drugs is through cell division inhibition, by acting on either DNA synthesis or function. By design, these treatments attack rapidly dividing cells. This results in the nonspecific killing of rapidly dividing normal cells as well as cancer cells and weakens the immune system. While several recent advances such as antiangiogenic compounds and kinase inhibitors hold promise, metastases are still largely incurable. Recently however, much interest has been focused on the normal physiological process of apoptosis, also known as programmed cell death. By selectively inducing this cell death mechanism in cancer cells, it may be possible to control and eliminate tumors [3, 4].

Drug resistance is typically classified as either inherent or acquired. The Goldie-Coldman hypothesis estimates that 1 in every 1,000,000 cancer cells is resistant to anticancer drugs due to inherent rates of mutation. This form of inherent drug resistance is developed before any exposure to an anticancer drug has taken place. Acquired drug resistance can be developed by the sublethal exposure of cells to anticancer drugs. This form of drug resistance is caused by the upregulation of cellular defense mechanisms. It is well known that levels of the major cellular antioxidant, GSH, is elevated in cancer cells to help buffer the high levels of reactive oxygen species (ROS). It is also well known that GSH is a strong detoxifier of anticancer drugs. Recently the protective effect of GSH against ionizing radiation has also been demonstrated in cancer stem cells [5]. The use of cancerostatic natural product may have the advantage of being an effective anticancer agent while not inducing drug resistance.

Apoptosis in normal cells can be induced by both extrinsic and intrinsic factors. Regardless of the method of induction, the sequence of events must culminate in the activation of the caspases. Extrinsic apoptosis is death receptor mediated while intrinsic apoptosis is mitochondria mediated and characterized by the rapid release of cytochrome c into the cytosol. The activation of either of these pathways by apoptotic stimuli is exceedingly complex. Attempts at trying to integrate the complexity of signaling events with the regulation of apoptosis has resulted in a dizzying array of possibilities which may or may not be physiologically significant. In spite of this complexity, the concept of perhaps cancer cell specific apoptosis remains a viable option [4].

Apoptosis in cancer cells is further complicated by the fact that they have broken apoptotic machinery. Parts of the process are either missing or functionally mutated, with the most notable being the tumor suppressor protein, p53. While at least 50% of cancers demonstrate either nonexistent or nonfunctional p53, cancer cells also contain various and numerous other apoptotic defects. This is consistent with the fact that cancer cells contain a high degree of cell to cell heterogeneity. Fortunately cancer cells can still undergo apoptosis and furthermore can be sensitized to do so through oxidation-reduction modulation [6].

Apoptosis has been widely reported to be modulated by changes in the oxidation-reduction state of the cell. Although the exact mechanism of action has not been elucidated, GSH and ROS have been strongly implicated. Levels of ROS are higher in cancer cells than in their normal counterparts [6]. Levels of GSH are also higher in cancer cells, by as much as 100% over those found in normal cells. Since excessive levels of ROS are toxic to cells, cancer cells with inherently higher levels of ROS should be more sensitive to further insult. However, evidence demonstrates by increasing the oxidative stress in cancer cells by adding ROS generators that apoptosis is not always induced [7].

GSH depletion has also been associated with the onset of apoptosis [7, 8, 9, 10]. Recent work has shown that GSH depletion is indeed necessary for the progression of apoptosis activated by both extrinsic and intrinsic pathways in cancer cells. Apoptosis by GSH depletion was found to be independent of ROS formation in cancer cells [7]. Depletion of GSH to levels approaching 5% of the controls in cancer cells leads to approximately 85% of the cells undergoing apoptosis. Therefore, compounds capable of depleting GSH levels in cancer cells should induce and/or sensitize cells to apoptosis.

Any protocol which is proposed for the chemotherapeutic treatment of cancer cells need to address the impact on cancer stem cells. Cancer stem cells are not easy to kill. Recent studies have found that cancer stem cells are particularly resistant to ionizing radiation. In addition, those cancer stem cells which contain relatively low levels of ROS were much more resistant to ionizing radiation compared to those with higher levels. Further study showed that the highly resistant cancer stem cells contained higher levels of GSH [5]. Thus as is the case in ordinary cancer cells, depleting GSH in cancer stem cells might induce or sensitize the cells to apoptosis.

Agents which deplete GSH selectively in cancer cells will have a significant effect on apoptosis. In order to achieve high levels of apoptotic induction GSH must be taken to very low intracellular levels, approaching 0-5% of the endogenous concentrations. Therefore, while cancer cell apoptosis can be achieved by significant GSH depletion alone, an additional cancerostatic agent is desirable to ensure the desired outcome.

A number of different approaches exist for reducing or depleting intracellular GSH. The primary mechanisms involve: 1) tying up GSH by forming a chemical complex between GSH and an electrophilic agent, 2) introducing an enzyme inhibitor to prevent GSH synthesis, and 3) raising GSH levels in order to activate enzyme feedback inhibition.

Dicarbonyl compounds have been studied for over 50 years because they possess cancerostatic properties at relatively low concentrations [11]. Of particular interest is the dicarbonyl compound, methylglyoxal (also known as pyruvaldehyde). Containing just a (3) carbon backbone, it is an extremely small, water soluble, and highly reactive compound. Due to its size and reactivity as an electron acceptor, it is a unique chemical and biochemical compound. Of critical importance are the following facts: 1) methylglyoxal is a naturally occurring metabolite in living systems, 2) methylglyoxal is catabolized to D-lactic acid by the glyoxalase enzyme system consisting of glyoxalase I and glyoxalase II, 3) methylglyoxal forms a nonenzymatic hemithioacetal adduct with GSH, and 4) methylglyoxal in the absence of glyoxalase II activity causes GSH to become trapped in the glyoxalase I intermediate S-lactoylglutathione thus depleting GSH levels.

Albert Szent-Gyorgyi in the 1960's, advanced the hypothesis that methylglyoxal might act as a natural brake on cell division by keeping cells in the resting state [12]. Subsequent work by his team and others showed that methylglyoxal treatment of cancer cells at levels of approximately 1-3 mM caused protein synthesis inhibition, arrested cell growth, and induced apoptosis [13]. Normal cells were not affected. These findings and much additional research over the intervening 40 years have supported and expanded this work. Of particular significance is the recent work of Manju Ray. She and her team have enhanced the understanding of the action of methylglyoxal at the cellular level, studied and reported the pharmacokinetics and toxicity, and conducted human cancer clinical trials [14, 15]. Additionally, there are a number of worldwide anecdotal cases of people self-administering methylglyoxal to treat cancer.

The majority of the early studies involving methylglyoxal and its cancerostatic action were conducted either with cultured cancer cells or with mice that had been innoculated intraperitoneally with cancer cells. This work consistently and repeatedly reported that concentrations approaching 3 mM were required to achieve 95-100% cell death. Methylgloxal administered orally cannot achieve these levels (216 mg/kg) in mammals based on pharmacokinetic bioavailability data. (IV) administration of methylglyoxal at these levels has not been reported.

Delivery of methylglyoxal to the bloodstream by any means results in its rapid catabolism. Pharmacokinetic studies in mice have shown that a single oral dose of methylglyoxal of 200 mg results in a peak blood concentration of approximately 20 nmol/cc or 0.02 mM at 4 hours with total clearance after 12 hours [16]. These levels are significantly lower than the 1-3 mM reported to induce significant cancer cell death. The presence of high levels of GSH and a full complement of glyoxalase enzymes makes delivering and maintaining pharmaceutical levels of methylglyoxal in the bloodstream unattainable. It is likely this is the reason that the limited number of previous clinical trials utilizing methylglyoxal to treat cancer have reported mixed results. Liposome systems have become a popular drug delivery platform for a number of important reasons [1, 2]. First, liposomes are composed of naturally occurring lipids which make them nontoxic and biodegradable. Second, liposomal drug encapsulation protects the active ingredients from the metabolic action of the body thereby preventing degradation and dilution. Third, liposomes can be modified to control their drug release rates. Fourth, in cancer, liposomes can be designed to migrate and preferentially accumulate at tumor sites as a result of their ability to extravagate through the large pores in the capillary endothelium. Thus liposomes may be custom designed for specific drug delivery needs by varying a number of critical variables including membrane chemical composition, particle size, surface treatment, and charge.

Prior artisans have explored a number of avenues in order to induce apoptosis in cancer cells by trying to deplete intracellular GSH levels. Such avenues have included the use of biologically active whey protein [17, 18], N-acetylcysteine [19], buthionine sulfoximine [20, 21, 22, 23, 24], and GSH complexing agents such as cinnamaldehyde [25], curcumin [26], quercetin [27], and isothiocyanates [28]. Results have demonstrated improvements in cancer patient survival times but not nearly to the extent necessary to be described as significant. Likewise recent chemical studies with oral methylglyoxal have increased survival rates and even resulted in some remission [14]. But again results have been variable. Recognition of challenges with delivering therapeutic levels of methylglyoxal have led researchers to form chemical conjugates to protect methylglyoxal in the bloodstream or introduce glyoxalase I inhibitors but also with less than hoped for results.

What is lacking in the art is: (1) a systemic therapy that can be used in conjunction with either surgery or radiation, (2) a therapy that leverages normal cellular physiological processes, (3) a therapy that can be given in nominal doses with compounds that, if they do come into contact with normal cells, are quickly metabolized to nontoxic substances, and (4) a therapy that causes little to no side effects in the patient.

The inventors of the current patent have research experience with both methylglyoxal and GSH dating back more than 30 years. Methylglyoxal was found to be missing in proliferative tissue but present in the organized tissue of origin [29] and GSH exhibited the opposite trend [30]. The latter studies also demonstrated the efficacy of using buthionine sulfoximine to lower the concentrations of GSH with biological consequences.

DESCRIPTION OF THE PRIOR ART

U.S. Pat. No. 4,238,500 (Szent-Gyorgyi et al) discloses novel chemical compounds having cytostatic, hypotensive and analgesic activity. The invention provides compositions consisting of conjugates of ascorbic acid and glyoxals, typically methylglyoxal, effective in the treatment of cancer. The invention claims inhibition of Ehrlich carcinoma and Sarcoma 180 (in both solid and ascitic forms) of approximately 36% and 96%, respectively, when administered intraperitoneally at 500 mg/kg daily. The reference fails to suggest potentiation of the ascorbic acid-methylglyoxal conjugate by GSH depletion or encapsulation of any sort to protect the active ingredients from degradation in the bloodstream and provides no examples to verify the effectiveness of administration other than intraperitoneally which is highly limited in practice. To our knowledge the art as described has never been practiced to treat cancer other than in vitro and on laboratory animals.

U.S. Pat. No. 5,476,966 (Anderson et al) discloses a method for decreasing glutathione in cells and tissues in order to sensitize the cancer cells to radiotherapy or chemotherapy. The invention proposes the use of S-(3-methyl)butyl homocysteine-SR-sulfoximine and S-(cyclohexyl)methyl homocysteine-SR-sulfoximine as having superior attributes to buthionine sulfoximine in combination with chemotherapy and radiotherapy for the treatment of cancer. The reference fails to suggest use in combination with dicarbonyls or encapsulation of any sort to protect the active ingredients from degradation in the bloodstream. The reference fails to protect normal tissues (kidney, liver, heart, brain etc.) from damaging GSH depletion. To our knowledge the art described has never been practiced to treat cancer other than in vitro and on laboratory animals.

U.S. Pat. No. 5,849,783 (Egyud) discloses a method for physically and chemically latentiated autobiotic compounds, particularly alpha ketoaldehydes, for the treatment of any disease. The alpha ketoaldehyde active compounds are either chemically conjugated or encapsulated in liposomes to protect them from degradation in the bloodstream. The reference fails to suggest combining alpha ketoaldehydes with a pretreatment to sensitize cancer cells by depleting GSH levels. The reference also fails to define the most appropriate liposomal particle size and surface treatment for increasing circulation times and masking the liposome from the immune system. To our knowledge the art as described has never been practiced to treat cancer other than in vitro and on laboratory animals.

U.S. Pat. No. 5,888,552 (Bounous et al) discloses a method for utilizing undenatured whey protein as a means of enhancing the immune system and as such providing resistance to chemically induced cancer and also the inhibition of cancer. The oral application of undenatured whey protein increases reduced glutathione levels in the bloodstream and normal tissues while lowering GSH levels in cancer cells through feedback inhibition. The reference fails to suggest the use of cancerostatic carbonyl compounds, preferably antitumor liposomal methylglyoxal, and their mechanism of action as a followup to the feedback inhibition of cancer cell GSH levels. The art has been described in the literature as an adjuvant to other treatments with mixed results.

U.S. Pat. No. 5,969,174 (Creighton et al) discloses an efficient method for generating cytotoxic inhibitors of glyoxalase I inside tumor cells via acyl-interchange with intracellular glutathione. The invention functions on the basis that, after the diethyl esters diffuse across the cell membrane, intracellular esterases catalytically deethylate the diethyl esters to give the inhibitory diacids. The inhibition of glyoxalase I allows for the intracellular accumulation of methylglyoxal to toxic levels in cancer cells. The reference lacks cancer cell specific targeting, relies on what is believed to be the very sporadic synthesis of methylglyoxal in cells, and does not reference GSH as a pretreatment. To our knowledge the art as described has never been used to treat cancer other than in vitro and on laboratory animals.

U.S. Pat. No. 6,407,071 (Rubin) discloses a composition for treating tumors comprising a combination of at least one oxidizing agent and at least one aldehyde or precursor thereof, which aldehyde forms an insoluble thiazoline with cysteine. Optionally, a compound which inhibits glutathione-s-transferase is included. The invention describes an oxidizing agent, preferably a phenolic, which is conjugated to a saccharide. An aldehyde is also described which is administered in free form or, alternatively, is also conjugated to a saccharide. The invention relies on the intracellular uptake of each of the conjugates, cleavage and activation by tyrosinase and saccharidase, and precipitation of a cysteine adduct as thiazolidine. In addition, adjusting the pH to 7.4 is recommended to assist in the selectivity of the conjugates toward tumors. Prior to treating patients, the tumor should be analyzed to, ensure high activity of both the tyrosinase and saccharidase enzymes. The reference lacks utility as a treatment for all cancers by relying on specific high enzyme activities in cancer cells, using nominal means of preferential cancer cell uptake, and relying on high levels of oxidizing agent and aldehyde administration at 5.0 mM and 10 mM respectively. To our knowledge the art as described has not been used to treat cancer other than in small trials.

U.S. Pat. No. 6,596,755 (Burman et al) describes an oral formulation of methylglyoxal and/or its imino acid conjugates for human use and methods for preparing the compositions. In particular the invention relates to compositions comprising methylgylyoxal and more particularly imino acid conjugates of methylglyoxal. The invention describes these conjugates and their use for treatment and suppression of malignant diseases. The preferred preparation method for methylglyoxal and methylglyoxal conjugates is lyophilization. The reference fails to give any pharmacokinetic data regarding the oral uptake of these lyophilized preparations or their therapeutic success. The reference lacks any pretreatment recommendation to sensitize cancer cells prior to administration. To our knowledge the art as described has not been used to treat cancer.

U.S. Pat. No. 6,613,793 (Burman et al) discloses the use of imino acid conjugates of methylglyoxal for the inhibition and/or treatment of cancer. The anticancer activity is attributed to the inhibition of the activity of glyceraldehyde-3-phosphate dehydrogenase and methylglyoxal conjugates are claimed to have antiangiogenic activity. The invention reports approximately 90% cancer cell kill rates at 10 mM concentrations of the methylglyoxal imino acid conjugate. The reference lacks any cancer cell specific targeting mechanism, relies on relatively high levels of the methylglyoxal imino acid conjugate to invoke less than a 40% inhibition of glyceraldehyde-3-phosphate dehydrogenase activity, describes no pretreatment mechanism to sensitize the cancer cells to the treatment, and delivers best case 90% kill rates at 10 mM concentrations of the conjugate. The art as described (oral free methylglyoxal plus ascorbic acid) has reported some success at doses of 25 mg/kg/day and 2000 mg, respectively, given in four divided doses in a study of 24 patients with various cancers.

U.S. Pat. App. 20080188541 (Ray) discloses a pharmaceutical composition and treatment method to reduce the proliferation of cancer or tumor cells, in which the combined active ingredients are methylglyoxal, ascorbic acid, creatine and melatonin. The study was initiated with the objective to resolve whether methylglyoxal is truly toxic in vivo and to reassess its therapeutic potential. The reference lacks any kind of pretreatment of cancer cells, specifically by oxidation-reduction modulation, to sensitize them to apoptosis. The reference does augment the cancerostatic action of methylglyoxal with ascorbic acid and creatine. The reference does not make use of antitumor liposomes or any other means to protect or target the delivery of the methylglyoxal agent. The art as described (oral free methylglyoxal, ascorbic acid, creatine and melatonin) has reported some success in two studies of 46 and 16 patients with various cancers.

WO 2007109184 (Hausheer) discloses the use of an effective amount of 2,2'-dithio-bis-ethane sulfonate, an acceptable salt thereof and/or an analogue thereof to cause augmentation of chemotherapeutic compounds. The reference lacks any tumor specific targeting or delivery system. The invention does not mention dicarbonyls or, more specifically, methylglyoxal as a chemotherapeutic agent. The reference does not make use of antitumor liposomes to protect or target the delivery of the augmenting agent. The art as described to our knowledge has not been used to treat cancer patients.

WO 2008082579 (Betin et al) describes a compound or an acceptable salt thereof that increases the oxidative stress in a cell, wherein the compound increases p38 activity and wherein the compound increases the cellular expression of Hsp70 and thereby augments the therapeutic activity of chemotherapeutic agents. The reference fails to give any tumor specific targeting or delivery system specifics. The reference does not make use of antitumor liposomes to protect or target cancer cells. The reference fails to mention dicarbonyls or, more specifically, methylglyoxal as a chemotherapeutic agent. The art as described to our knowledge has been used to treat a limited number of cancer patients with some limited adjuvant success.

WO 2010028503 (Droge et al) describes a cysteine-rich whey derived protein formulation which resulted in increased cancer patient survival when used in conjunction with chemotherapy or radiation treatment. The cysteine-rich whey protein formulation was administered orally at from 5-30 g/day, preferably about 13 g/day. The invention, when used in conjunction with chemotherapy or radiation, resulted in increased survival times and quality of life. The reference does not mention antitumor liposomal methylglyoxal as a chemotherapeutic agent. The art as described has been used to treat cancer as an adjuvant in approximately 100 patients.

OBJECTIVES OF THE INVENTION

The following objectives serve to form the basis for the present invention.

To provide a protocol for the treatment of all cancers which covers all types and stages in all animals including mammals and humans.

To provide a protocol for the treatment of all cancers which is compatible with the use of surgery or radiation therapy.

To provide a protocol for the treatment of all cancers which uses a normal physiological process.

To provide a protocol for the treatment of all cancers which addresses the issues revolving around first order kinetics of chemotherapeutic agents.

To provide a protocol for the treatment of all cancers which addresses the issues surrounding the elimination of cancer stem cells.

To provide a protocol for the treatment of all cancers which uses naturally occurring metabolites when possible.

To provide a protocol for the treatment of all cancers which greatly minimizes the side effects to the patient.

To provide a protocol for the treatment of all cancers which does not compromise the immune system.

To provide a protocol for the treatment of all cancers which is not susceptible to the development of resistance.

To provide a protocol for the treatment of all cancers which addresses the issues surrounding pharmacokinetics, particularly bioavailability and distribution.

To provide a protocol for the treatment of all cancers which addresses the issues surrounding metastasis.

SUMMARY OF THE INVENTION

The present invention is directed to the overall objective of controlling and eliminating all cancer cells, including cancer stem cells and those that have metastasized, while causing the patient minimal side effects. The invention purposely leverages the well-documented cancerostatic properties of dicarbonyl compounds, particularly the naturally occurring metabolite, methylglyoxal. Since the ubiquitous glyoxalase enzyme system rapidly metabolizes methylglyoxal in the bloodstream, pharmacokinetic protection is necessary and is provided by means of liposomal encapsulation. By further engineering a number of critical physiochemical properties of liposomes, the active dicarbonyl payload is predominantly delivered to the tumor sites.

Although the cancerostatic properties of dicarbonyls are well known, have been studied quite extensively, and are effective at low concentration, the total elimination of cancer cells (either disseminated or solid mass) by chemotherapeutic agents, follows first order kinetics. Thus if a tumor mass contains $10^{12}$ malignant cells and 99.99% are killed, then $10^8$ malignant cells would remain. Although the patient at this point would be diagnosed as in remission, any of the $10^8$ malignant cells could cause a relapse in the disease. This is in fact likely due to the high probability that the $10^8$ population of remaining malignant cells could be harboring cancer stem cells.

The present invention addresses these added challenges by sensitizing cancer cells to apoptosis by dicarbonyls through oxidation-reduction potentiation. The administration of GSH depleting agents, acting by means of a number of different mechanisms, causes cancer cell and cancer stem cell sensitization and subsequent apoptosis. By depleting GSH levels in this way, the cancerostatic dicarbonyls achieve a much higher kill rate and, because they are natural metabolites, do not induce drug resistance. Continued administration of the pretreatment and treatment eliminates the tumor mass. Intermittent administration of either the free dicarbonyl or a nutraceutical liposome formulation quenches any metastasis through systemic delivery of the free drug.

DETAILED DESCRIPTION OF THE INVENTION

The objectives of the invention are stated in a previous section of this patent. The cancer treatment protocol disclosed here provides a technical solution to each of these objectives as described below.

Current chemotherapy is hampered by its toxicity and side effects. However the basic concept of systemic administration makes chemotherapy theoretically capable of treating all types and stages of cancer by being able to access all cells in all tissues within the body. The treatment protocol disclosed here relies on a systemic approach in order to access all cells in order to achieve the objective of treating all types and stages of cancer. While cancer can be treated at all stages with the disclosed protocol, it should be mentioned that tumor growth which has reached the point that critical organs are compromised and marginally functioning is likely past the point of return to health.

Surgery and radiation therapy, on the other hand, are not applicable to all types and stages of cancer. This is due mainly to tumor inaccessibility, precision of administration, development of resistance, and inability to treat disseminated or metastasized cancers. Despite these limitations, the present invention acknowledges the beneficial role of surgery and radiation in treating certain cancers. The treatment protocol disclosed here is an appropriate adjuvant to eliminate any remaining cells at the tumor sites or metastasized cells for all cancers that have been treated by either surgery or radiation. The treatment protocol achieves the objective of being compatible with surgery and radiation. Additionally, the protocol sensitizes cancer cells to radiation.

To be effective against all cancers, the treatment ideally should be based on leveraging a normal and ubiquitous physiological process. Apoptosis, also known as programmed cell death, is a normal and ubiquitous physiological process whereby an organism rids itself of unneeded or undesirable cells. The process is used during development, maintenance of cell homeostasis and in response to disease. A disruption in the normal process of apoptosis appears to be associated with diseases including cancer. Intuitively, the lack of an appropriate amount of apoptosis (cell death) is likely to be associated with cancer. The treatment protocol disclosed here relies chiefly, but not exclusively, on selectively inducing apoptosis in cancer cells to achieve the objective of leveraging a normal physiological process.

In normal cells, the extrinsic and intrinsic apoptotic signaling pathways are highly complex and redundant. In cancer cells, this highly complex machinery is broken. Since the number of players involved in the apoptotic process is high, the number of combinations and permutations of apoptotic defects is huge. This is consistent with the fact that cancer cells exhibit a high degree of cell to cell heterogeneity. Nevertheless, despite defective apoptotic machinery, cancer cells can still undergo apoptosis and additionally can be sensitized to apoptosis through oxidation-reduction modulation.

Oxidation-reduction modulation as described in the present invention refers to the depletion of intracellular GSH levels specifically in cancer cells and cancer stem cells. The depletion of intracellular GSH levels specifically in cancer cells induces some apoptosis on its own. Those remaining cancer or cancer stem cells find themselves highly sensitized to the addition of subsequent apoptotic compounds.

The depletion of GSH in cancer and cancer stem cells by a number of different mechanisms and agents forms the pretreatment step of the present invention. The pretreatment stage can be implemented through: 1) chemical complexing of intracellular GSH by electrophilic agents, 2) inhibition of intracellular GSH synthesis, and 3) feedback inhibition of intracellular GSH synthesis. All or any of these mechanisms with their corresponding active agents may be utilized as the pretreatment step. The pretreatment step allows for much higher kill rates and with continued administration helps to achieve the objective of addressing the issues associated with the first order kinetics of chemotherapy. The pretreatment step also addresses the objective of killing cancer stem cells which have been shown to be protected from apoptosis by high levels of GSH.

The pretreatment step may be achieved by chemically complexing intracellular GSH with electrophilic agents. Agents which form chemical complexes with GSH comprise a wide range of electrophilic compounds too numerous to list. This invention identifies but is not limited to cinnamaldehyde, curcumin, quercetin and isothiocyanates. These compounds are known to complex with GSH in biological systems causing a lowering of their GSH levels in blood plasma and tissues. While many compounds will complex with GSH these four are noted due to the amount of research on each and their generally recognized low toxicity in living systems. Oral administration of these compounds does not lead to selective depletion of GSH in cancer or cancer stem cells. Accordingly, this invention recommends that these compounds be encapsulated in antitumor liposomes for cancer cell targeted delivery. The selection of these compounds for the pretreatment step achieves the objective of using naturally occurring compounds whenever possible and of minimizing side effects to the patient.

The pretreatment step may also be achieved by the inhibition of intracellular GSH synthesis. Buthioinine sulfoximine or its derivatives are typically used to inhibit the first enzyme, gamma-glutamyl sytnthetase, in the synthesis of GSH. Compounds like buthioinine sulfoximine have been studied extensive in living systems as a means of depleting intracellular GSH levels. Most of this work has been carried out using cell cultures although recent human clinical studies have incorporated buthioinine sulfoximine as an adjuvant in conjunction with standard chemotherapy. Since direct (IV) administration of buthioinine sulfoximine or its derivatives to the bloodstream does not specifically deplete GSH levels in cancer cells, this inventions recommends encapsulation in antitumor liposomes. Antitumor liposomal buthioinine sulfoximine and its derivatives or any other inhibitor of GSH synthesis are identified by the present invention as a pretreatment choice. Although buthioinine sulfoximine and its derivatives are not naturally occurring substances, (IV) administration of buthioinine sulfoximine at levels of 3.0 grams/$m^2$ has shown no deleterious effects.

The pretreatment step may also be achieved by feedback inhibition of intracellular GSH synthesis. This is accomplished by increasing the concentration of intracellular GSH in cancer and cancer stem cells. The resulting elevated intracellular levels inhibit the synthesis of any additional intracellular GSH. This causes the GSH levels to fall below normal levels and thus results in depletion until further synthesis is requested. GSH is poorly transported across the cell membrane from the plasma. Thus intracellular synthesis is required which depends on the availability of an adequate supply of constituent amino acids, chiefly cysteine or cystine residues. This invention describes the use of N-acetyl cysteine and biologically active whey protein as two means of achieving feedback inhibition of GSH synthesis. N-acetyl cysteine has has been shown to increase both intracellular and extracellular GSH concentrations. Biologically active whey protein also increases GSH levels in both normal cells and cancer cells and simultaneously boosts the immune system. Biologically active whey protein and N-acetyl cysteine are both administered orally. Biologically active whey protein gradually increases GSH levels over the first weeks of administration whereas N-acetyl cysteine spikes the levels within hours. Both applications serve to raise GSH levels and then deplete them through feedback inhibition particularly in cancer cells. Increases in GSH in normal cells caused by this pretreatment are tightly controlled and any excess is transported out of the cell. The use of either N-acetyl cysteine or biologically active whey protein, achieves the objectives of using naturally occurring compounds whenever possible to build the immune system as opposed to compromising it.

The cancerostatic effect of dicarbonyls has been known and studied for over 50 years with the ketoaldehydes being the focus of much of this research effort. Indeed the anticancer, antiviral drug Kethoxal (3-ethoxy 2-ketobutyraldehyde) has been marketed by the Upjohn Company for decades. Methylglyoxal, however, has gained the most attention within this group due to the fact that it: 1) is a byproduct of glycolysis, 2) has an enzyme associated with its synthesis, 3) non-enzymatically forms a hemithioacetal with GSH, 4) is rapidly catabolized by the glyoxalase enzyme system to D-lactic acid, and 5) appears to be ubiquitous throughout living systems.

The present invention identifies (but is not limited to) methylglyoxal as the preferred choice of cancerostatic dicarbonyl for the treatment phase of the disclosed protocol. This choice is based on the fact that methylglyoxal exists as a normal metabolite in most living systems and therefore has a well-defined metabolism while also possessing strong and specific cancerostatic properties. This choice for the treatment step achieves the objectives of: 1) using naturally occurring compounds, 2) minimizing side effects to the patient, 3) not compromisizing the immune system, 4) being effective against all cancers in all animals, 5) being effective against cancer stem cells, and 6) not inducing drug resistance in cancer cells since it is a natural product.

The effect of methylglyoxal concentration on the growth rate of cultured lymphoma cells is shown below. The cells used were murine B cell lymphoma cell line (A20; ATCC#TIB-208). Cells labeled A20 were untreated cells that were passed through their regular media. A20 Methylglyoxal Reversed cells had undergone 3 passages in media containing 1 mM methylglyoxal followed by 3 passages in regular media before use. A20 Methylglyoxal P6 cells had 6 passages in media containing 1 mM methylglyoxal before use. At the start of the experiment harvested cells were incubated with DNA precursor tritiated thymidine in media containing the various concentrations of methylglyoxal for 12 hours, then harvested and counted in a scintillation counter. The count data in cpm reflect the growth rate of the cells in the presence of the various methylglyoxal concentrations. Relevant data from this in vitro study are presented here.

| | Methylglyoxal Concentration | | | | | |
|---|---|---|---|---|---|---|
| Cell Line | 0 mM | 0.3 mM | 0.6 mM | 1.2 mM | 2.5 mM | 5.0 mM |
| 1. A20 | | | | | | |
| [1]Mean, cpm | 34,286 | 36,289 | 30,119 | 275 | 6 | 8 |
| SD | 3,382 | 2,961 | 1,688 | 47 | 1 | 3 |
| 2. A20 1 mM Methylglyoxal Reversed P3 | | | | | | |
| [1]Mean, cpm | 35,083 | 34,220 | 33,927 | 587 | 7 | 12 |
| SD | 2,297 | 2,138 | 420 | 63 | 1 | 4 |
| 3. A20 1 mM Methylglyoxal P6 | | | | | | |
| [1]Mean, cpm | 34,286 | 36,001 | 35,157 | 1,470 | 24 | 9 |
| SD | 3,382 | 1,448 | 1,091 | 447 | 5 | 2 |

[1]triplicates

The data from the foregoing in vitro investigation show that the lymphoma cells are able to survive the 1 mM methylglyoxal that they encountered in the A20 Methylglyoxal Reversal and A20 Methylglyoxal P6 cases. However, like the untreated A20 cells which had not encountered methylglyoxal until the start of the experiment, 1.2 mM methylglyoxal severely slowed their growth rate, falling to less than 0.1% of the controls at the 2.5 mM and 5.0 mM levels. Furthermore, there is no evidence that the A20 Methylglyoxal Reversal and A20 Methylglyoxal P6 cells developed any significant resistance to methylglyoxal.

The present invention leverages methylglyoxal to control and eliminate cancer cells through the use of all of the following mechanisms. Methylglyoxal is known to induce apoptosis by: 1) inhibiting protein synthesis, 2) forming adducts with nucleic acids, 3) increasing intracellular oxidative stress by complexing nonenzymatically with GSH, 4) reducing cancer cell ATP production by inhibiting mitochondrial respiration, and 5) inhibiting glutathione reductase activity. By binding to cancer cell surface sulfhydryl and arginine groups it further exposes these cells to the immune system. In addition, methylglyoxal has been shown to induce a specific immune response toward cancer cells. Since cancer cells contain very low levels or lack entirely glyoxalase II activity, the current patent adds depletion of GSH as an additional mechanism. This mechanism further promotes apoptosis by trapping GSH in the glyoxalase I reaction product S-lactoylglutathione and not allowing it to be recycled.

Delivery of the treatment portion of the disclosed protocol using the preferred methylglyoxal is complicated by the pharmacokinetics of oral administration and a high level of catabolism within the bloodstream by the glyoxalases. A limited number of studies on the oral uptake of methylglyoxal have demonstrated less than 5% uptake. Once in the bloodstream, the circulation half-life has been estimated to be from 30 to 120 minutes. Although the $V_{max}$ for other ketoaldehydes with the glyoxalases is lower than methylglyoxal, so too is their therapeutic index relative to inducing apoptosis in cancer cells. Thus while methylglyoxal remains the ketoaldehyde of choice, further steps must be taken to ensure adequate bioavailability of the agent in the bloodstream.

The recently acquired ability to custom engineer the critical parameters involved in liposome construction has allowed this technology to be greatly expanded for use as a drug delivery platform. Liposomal encapsulation of the active ingredient, whether it be the pretreatment or treatment, greatly enhances its bioavailability and distribution. As a result, this greatly enhances its effectiveness. The present invention utilizes liposomal technology to: 1) protect the active pretreatment or treatment compound from degradation by the bloodstream, and 2) target the active ingredient to the tumor sites. The use of liposomal technology allows this patent to achieve the objective of sufficient bioavailability and targeted distribution.

This patent makes widespread use of antitumor liposomes. These structures are first and foremost defined by their particle size. Antitumor liposomes which migrate to and extravasate into tumor specific regions are typically within the range of 50 to 150 nm. The chemical composition of these structures varies, but typically contains an amount of cholesterol sufficient to give the desired mechanical stability. The surface is treated to mask the liposome to macrophage response and elimination, typically by adding propylene glycol known as pegylation. The surface may be further treated with an antibody to heighten the level of target specificity. While the described parameters are some of the key features of antitumor liposomes, this patent does not in any way limit their description to exclusively this list.

This patent also utilizes nutraceutical liposomes. These structures are chiefly defined by their particle size which generally are in the range of 250 to 500 nm. They allow for oral administration of the pretreatment or treatment compounds to the bloodstream, which helps increase the bioavailability and mask the taste of these ingredients. Nutraceutical liposome delivery, particularly of methylglyoxal, provides an easy means for self-administering an ongoing treatment to address potential metastasis.

Pretreatment compounds that chemically complex with GSH that are named in this patent are cinnamaldehyde, curcumin, quercetin, and isothiocyanates. The patent does not limit the list to just these electrophilic compounds. Delivery of these compounds is best achieved through encapsulation in antitumor liposomes. While all may be delivered orally, results should be greatly enhanced by the targeted delivery.

Pretreatment compounds that inhibit the synthesis of GSH that are named in this patent are buthionine sufoximine and its derivatives. The patent does not limit the list to just these GSH synthesis inhibitors. Delivery of these compounds is best achieved through encapsulation in antitumor liposomes. While delivery of the free compound by (IV) is possible, there is no targeting of the effect specifically to cancer cells. Consequently, overall system GSH can become depleted also with the associated complications including impact on the immune system.

Pretreatment compounds that trigger feedback inhibition of GSH synthesis that are named in this patent are N-acetyl cysteine and biologically active whey protein. The patent does not limit the list to just these substances capable of increasing GSH levels in cancer cells whereby feedback inhibition subsequently causes depletion. Delivery of the mentioned compounds is best achieved through oral administration.

The treatment to induce apoptosis in cancer cells is preferred by this patent to be the cancerostatic dicarbonyl, methylglyoxal. The patent does not limit the list of cancerostatic dicarbonyls to just methylglyoxal. Delivery of this compound is dependent on the type of cancer being treated and the stage of the treatment. Delivery of methylglyoxal can be by antitumor liposome, by nutraceutical liposome, or as free methylglyoxal.

Treatment of highly vascular solid mass tumors is preferred to be by antitumor liposome methylglyoxal for the treatment portion of the protocol. This patent does not limit the treatment of these tumors to just this compound or form of delivery.

Treatment of low vascular solid mass tumors can be by antitumor liposome methylglyoxal, by nutraceutical liposomal methylglyoxal or as free methylglyoxal for the treatment portion of the protocol. This patent does not limit the treatment of these tumors to just this compound or forms of delivery.

Treatment of blood cancers can be by antitumor liposomal methylglyoxal in combination with nutraceutical liposomal methylglyoxal or free methylglyoxal for the treatment portion of the protocol. This patent does not limit the treatment of blood cancers to just this compound or form of delivery.

Treatment of brain cancers can be by nutraceutical liposomal methylglyoxal or free methylglyoxal for the treatment portion of the protocol. This patent does not limit the treatment of brain cancers to just this compound or forms of delivery.

In order to help prevent, control and eliminate any possible metastasis during treatment when antitumor liposomal methylglyoxal and/or nutraceutical liposomal methylglyoxal. The use of free methylglyoxal and nutraceutical liposomal methylglyoxal will allow the scavenging in the bloodstream of any metastatic cells or cell clusters which have broken free from the primary tumor site. This achieves the objective of addressing metastasis.

Since many cancers possess a predisposition for aberrant genetic expression, the tendency for recurrence can be high.

The present patent addresses this issue by recommending a maintenance schedule to ensure continued good health. A typical maintenance schedule would include a daily biologically active whey protein supplement in addition to an occasional (1-3 times per week) supplement of methylglyoxal.

PREFERRED EMBODIMENTS OF THE INVENTION

The following examples are given for the purpose of illustrating some typical embodiments of the invention and are not meant to limit the presentation in any way. The protocol, which is the novel aspect of the present invention, combines a cancer cell specific intracellular GSH depleting agent with a cancerostatic dicarbonyl compound to treat cancer. The intracellular GSH depleting agents, which make up the pretreatment step, may be from any of the classes or mechanisms described previously. The cancerostatic dicarbonyl compound which makes up the treatment step is not limited to, but is preferred to be, methylglyoxal. The preferred delivery system is dependent upon the nature of the pretreatment compound, the nature of the treatment compound, and the type of cancer. Although oral administration is preferred due to the ease of administration and is used whenever possible, it may be precluded when bioavailability and targeted distribution needs must be met in order to be therapeutically effective.

Highly vascular solid tumors present the opportunity to employ antitumor liposomes for the delivery of both the pretreatment and treatment steps of the protocol.

The preferred pretreatment step for highly vascular solid tumors is antitumor liposomal buthionine sulfoximine and/or any of its derivatives. The high vascularity allows the antitumor liposomes to extravasate the extracellular region of the tumor and deliver the active agent, in this case buthionine sulfoximine, to the cancer cells to sensitize them to apoptosis. The preferred route of administration for the antitumor liposomal buthionine sulfoximine is (IV).

Additional pretreatment options include using antitumor liposomal cinnamaldehyde, curcumin, isothiocyanates, quercetin or any other compound from the class of electrophilic agents which chemically complex with GSH. The preferred route of administration of these antitumor liposomal formulations is (IV). In addition oral N-acetylcysteine and biologically active whey protein may be used.

The preferred treatment step for highly vascular solid tumors is antitumor liposomal methylglyoxal. The preferred route of administration for the antitumor liposomal methylglyoxal is (IV). Administration of oral free methylglyoxal or nutraceutical liposomal methylglyoxal between treatments addresses potential metastasis.

Low vascular solid tumors present the opportunity to employ antitumor liposomes for the delivery of both the pretreatment and treatment steps of the protocol. Antitumor liposomes can provide longer circulation times and release rates, thereby increasing the amount of active pharmaceutical ingredient accumulation at the tumor site.

The preferred pretreatment step for low vascular solid tumors is antitumor liposomal buthionine sulfoximine and/or its derivatives. The preferred route of aministration is (IV).

Additional pretreatment options include using antitumor liposomal cinnamaldehyde, curcumin, isothiocyanates, quercetin, or any other compound from the class of electrophilic agents which chemically complex with GSH. The preferred route of administration of these antitumor liposomal forumations is (IV). In addition, oral N-acetylcysteine or biologically active whey protein may be used.

The preferred treatment step for low vascular solid tumors is antitumor liposomal methylglyoxal. The preferred route of administration is (IV). Administration of oral free methylglyoxal or nutraceutical liposomal methylglyoxal between treatments enhances the pharmacokinetic distribution issue of low vascularity and address potential metastasis.

Hematological neoplasms of the lymphomic or leukemic variety present the opportunity for use of antitumor liposomal nutraceutical, liposomal, and free compound pretreatment and treatment protocols.

Lymphomas which begin in the lymphatic cells of the immune system and present as a solid tumor of lymphoid cells may be treated by means of antitumor liposomes for the pretreatment and treatment steps.

The preferred pretreatment step for lymphomas which have presented as a solid tumor is antitumor liposomal buthionine sulfoximine and/or its derivatives. The preferred route of administration is (IV).

Additional pretreatment options include using antitumor liposomal cinnamaldehyde, curcumin, isothiocyanates, quercetin, or any other compound from the class of electrophilic agents which chemically complex with GSH. The preferred route of administration of these antitumor liposomal formulations is (IV). In addition, oral N-acetylcysteine or biologically active whey protein may be used.

The preferred treatment step for lymphomas which have presented as solid tumors is antitumor liposomal methylglyoxal. The preferred route of administration is (IV). Administration of oral free methylglyoxal or nutraceutical liposomal methylglyoxal between treatments addresses any lymphatic cells which may be freely circulating or lodged within the lymph system which have as of yet not presented as a solid tumor mass.

Leukemias whether acute or chronic can be approached from a targeted antitumor liposomal pretreatment and treatment protocol, a nutraceutical liposomal pretreatment and treatment protocol, and nonliposomal treatments address the systemic complications.

The preferred pretreatment step for leukemias to address the marrow source is antitumor liposomal buthionine sulfoximine and/or its derivatives. The pretreatment step focuses on sensitizing the cells within the marrow to apoptosis. The preferred route of administration is (IV).

Additional pretreatment options which focus on sensitizing the cells within the marrow include using antitumor liposomal cinnamaldehyde, curcumin, isothiocyanates, quercetin, or any other compound from the class of electrophilic agents which chemically complex with GSH. The preferred route of administration of these antitumor liposomal formulations is (IV). In addition, oral N-acetylcysteine or biologically active whey protein may be used.

The preferred pretreatment step for leukemias to address the systemic complication is nonliposomal buthionine sulfoximine administered by (IV). Additional pretreatment options for the systemic complication include using oral nutraceutical liposomal cinnamaldehyde, curcumin, isothiocyanates, quercetin, or any other compounds from the class of electrophilic agents which chemically complex with GSH. Also, oral N-acetylcysteine or biologically active whey protein may be used.

The preferred treatment step for leukemias is antitumor liposomal methylglyoxal. This treatment step induces apoptosis in the cancer cells within the marrow. The preferred route of administration is (IV). The preferred treatment step for the systemic complications is (IV) free methylglyoxal or either oral free methylglyoxal or nutraceutical liposomal methylglyoxal.

Brain tumors present the added complication of transport across the blood brain barrier. The inability of antitumor liposomes to cross the blood-brain barrier to any appreciable extent causes them to be of limited value. Therefore, the administration of the pretreatment and treatment steps is carried out by application of either the free compounds or the compounds encapsulated in nutraceutical liposomes.

The preferred pretreatment for brain tumors is free buthionine sulfoximine and/or its derivatives derivatives, especially buthionine sulfoximine ethyl ester. The preferred route of administration is (IV). Additional pretreatment options for brain tumors include (IV) administration of free cinnamaldehyde, curcumin, isothiocyanates, quercetin, or any other compounds from the class of electrophilic agents which chemically complex with GSH. Alternatively, nutraceutical liposomal cinnamaldehyde, curcumin, isothiocyanates, or quercetin may be orally administered. Also oral N-acetylcysteine or biologically active whey protein may be used.

The preferred treatment step for brain tumors is methylglyoxal. The preferred route of administration is (IV) with free methylgyoxal.

What is claimed is:

1. A method of treating an individual suffering from cancer, comprising:

1) a pretreatment step to cause oxidative stress by inhibiting gamma-glutamylcysteine synthetase activity which in turn sensitizes the cancer to apoptosis by dicarbonyls, comprising administration of a gamma-glutamylcysteine synthetase inhibitor to the cancer; and
2) a subsequent treatment step to cause apoptosis of the cancer, comprising administration of cancerostatic dicarbonyl compound to the cancer, wherein the pretreatment step potentiates the effectiveness of the cancerostatic dicarbonyl compound, thereby killing and inhibiting the growth of the cancer, and treating the individual.

2. The method of claim 1, wherein the gamma-glutamylcysteine inhibitor is administered in the form of liposomes encapsulating the gamma-glutamylcysteine synthetase inhibitor.

3. The method of claim 1, wherein the cancerostatic dicarbonyl compound is administered in the form of liposomes encapsulating the cancerostatic dicarbonyl compound.

4. The method of claim 1, wherein the gamma-glutamylcysteine synthetase inhibitor is buthionine sulfoximine.

5. The method of claim 1, wherein the cancerostatic dicarbonyl compound is methylglyoxal.

* * * * *